(12) United States Patent
Lind

(10) Patent No.: US 6,337,741 B1
(45) Date of Patent: Jan. 8, 2002

(54) SENSOR SYSTEM FOR MEASURING THE LIGHT ABSORPTION IN A TARGET

(75) Inventor: Steinar Lind, Nittedal (NO)

(73) Assignee: Simrad Optronics ASA, Oslo (NO)

( * ) Notice: Subject to any disclaimer, the term of this patent is extended or adjusted under 35 U.S.C. 154(b) by 0 days.

(21) Appl. No.: 09/622,670

(22) PCT Filed: Feb. 23, 1999

(86) PCT No.: PCT/NO99/00059

§ 371 Date: Aug. 22, 2000

§ 102(e) Date: Aug. 22, 2000

(87) PCT Pub. No.: WO99/44039

PCT Pub. Date: Sep. 2, 1999

(30) Foreign Application Priority Data

Feb. 26, 1998 (NO) .............................................. 980828

(51) Int. Cl.⁷ .............................................. G01N 21/00
(52) U.S. Cl. ..................................................... 356/437
(58) Field of Search ................................. 356/432, 433, 356/434, 435, 436, 437, 438, 439, 440; 250/343, 344, 345, 373, 573, 574, 575, 576

(56) References Cited

U.S. PATENT DOCUMENTS

| | | | | |
|---|---|---|---|---|
| 3,885,162 A | * | 5/1975 | Geertz | 250/573 |
| 4,798,965 A | * | 1/1989 | Fetzer et al. | 356/436 |
| 5,009,064 A | * | 4/1991 | Grob et al. | 60/276 |
| 6,122,042 A | * | 9/2000 | Wunderman et al. | 356/73 |

* cited by examiner

Primary Examiner—Hoa Q. Pham
(74) Attorney, Agent, or Firm—Rothwell, Figg Ernst & Manbeck

(57) ABSTRACT

A sensor system for measuring the light absorption in a target, e.g. a gas, comprising a first and a second optical transducer, one of which being a light source and the other being a light receiver, adapted to emit and detect, respectively, light within a chosen range of wavelengths, a partially reflective beam splitter adapted to reflect light to or from said first transducer, and to transmit light to or from said second transducer, and a lens or a group of lenses with a chosen focal length transmitting light to or from said transducers. The beam splitter comprises a first reflecting part and a second transmitting part being different from said first part, and a shield being positioned between said transmitting part and said first transducer.

12 Claims, 1 Drawing Sheet

SENSOR SYSTEM FOR MEASURING THE LIGHT ABSORPTION IN A TARGET

BACKGROUND OF THE INVENTION

1. Field of the Invention

This invention relates to a sensor system for measuring the light absorption in a target, e.g. a gas, comprising a first and a second optical transducer, one of which being a light source and the other being a light receiver, adapted to emit and detect, respectively, light within a chosen range of wavelengths, a partially reflective beam splitter adapted to reflect light to or from said first transducer, and to transmit light to or from said second transducer, and a lens or a group of lenses with a chosen focal length transmitting light to or from said transducers.

2. Description of the Related Art

Finding contents of a gas mixture is often done by transmitting a infrared beam with a known spectrum over a chosen path to a receiver. The receiver and instruments connected thereto are adapted to identify the wavelengths being absorbed by the gas mixture, and thereby to identify the elements present in the mixture.

The method is especially interesting when monitoring the atmosphere in e.g. a factory hall as a warning system for poisonous gases, explosion danger etc.

Usually the transmitter and receiver are separate units, and the transmitted light beam is aimed at the receiver. It is, however, difficult to obtain good mechanical stability in combination with angular adjustments with high precision.

To avoid the use of cables between the source and the receiver, and thus potential electrical noise, the measuring beam is also used to synchronize the receiver. This, however, results in a high probability for external disturbances in the measuring path, such as sunlight and blocking of the path.

This solution does not give any possibilities for monitoring the spectral distribution of the emitted radiation, and thus variations in this may also give 35 erroneous measurements. Often such instruments are connected to systems which close down an industrial process or oil/gas-production at a gas alarm. Production stops related to false alarms are expensive and reduces the operators confidence in the system. Therefore it is equally important that such instruments do not generate false alarms, as it is that all gas leaks are detected.

Another known type of gas sensors comprise the transmitter and the receiver in the same housing. The light beams is sent via a retro-reflector back to the receiver. Because of the requirement for high contrast in the received signal and the large amplitude of the transmitted beam compared to the received beam, the transmitted and the received beams have to be completely separated. This is normally done by using separate lens systems for the two transducers type, and keeping the transducers in separate compartments in the housing. This, however, is a complicated and voluminous solution, making the instrument large and expensive.

The instrument according to this invention is based on the solution with both transducers, the transmitter and the receiver, in the same housing. The transducers use the same collimating lens system directing the emitted beam towards a retro reflector. Thus all optical components may be integrated in the same compact unit, thus being adapted to use in a compact and robust instrument. Two sources, e.g. one generating the radiation used in the measurements and the other emitting a reference wavelength, may be integrated in the instrument. Also it is possible to measure the radiation before it is emitted into the beam path. This way an instrument may be constructed which does not produce erroneous measurements because of disturbances in the path or changes in the source.

A similar system is described in GB 2.219.656, comprising a transmitter and a receiver, both being directed towards a lens through a beam splitter. The retro reflector simplifies the alignment of the optical system, but the described system does, however have a disadvantage in that light transmitted from the transmitter will be reflected internally in the instrument, and affect the receiver.

SUMMARY OF THE INVENTION

Since the received radiation is in the range of two to three decades weaker than the emitted radiation it is impossible to reduce the internal reflections sufficiently to obtain acceptable results. To avoid this the sensor system according to the invention comprises a beam splitter including a first reflecting part and a second transmitting part being different from said first part, and a shield being positioned between said transmitting part and said first transducer.

BRIEF DESCRIPTION OF THE DRAWINGS

The invention will be described in detail below with reference to the accompanying drawing, which illustrate one example of an embodiment of the invention.

DETAILED DESCRIPTION OF THE PREFERRED EMBODIMENTS

Figure 1:
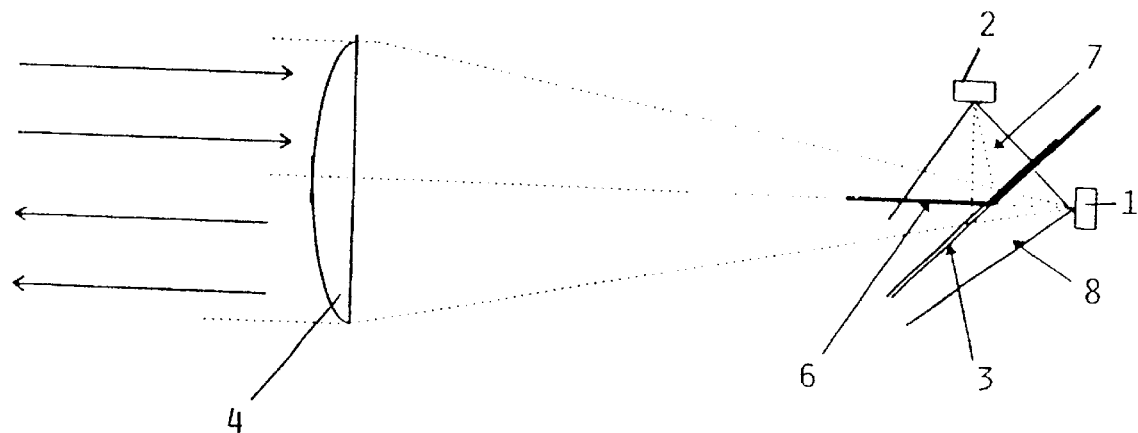
FIG. 1 shows a cross section of a sensor system according to the invention.

In FIG. 1 the sensor system comprises a transmitter 1 and a receiver 2, transmitting and receiving, respectively, radiation through a lens 4 and a beam splitter 3.

The transducers may be of any available type, the spectra, output and sensitivity depending on intended use of the system. The lens or lens system is chosen according to the frequency range of the system and the required aperture.

In the illustrated embodiment radiation is transmitted from the transmitter 1, through the beam splitter 3 and through the lens or lens system 4, which preferably collimates the beam. The transmitter is preferably positioned in or close to the focal point of the lens or lens system 4 to maximize the transferring of radiation.

Received radiation is focused by the lens towards the transducers 1, 2. The radiation is reflected by the beam splitter 3 to the receiver 2, which also is positioned in or close to the focal point of the lens 4. The positions of the transmitter and the receiver are of course interchangeable.

Figure 2:
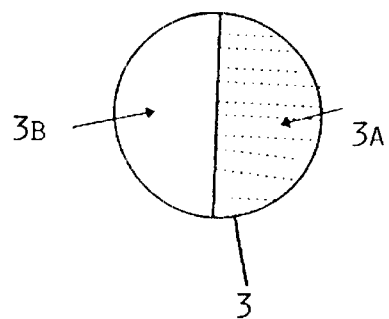
FIG. 2 shows a detail of a beam splitter comprised in the sensor system.

According to the invention the beam splitter includes an essentially totally reflecting part 3A and a transparent part 3B (see FIG. 2). The-transparent part may be omitted, the beam splitter thus being a mirror partially 35 obstructing the radiation directed from the transmitter through the lens, and reflecting a part of the radiation received through the lens towards the receiver. The reflecting part of the beam splitter is preferably the part closest to the receiver, but other, more complicated constellations are of course possible. Also, the ratio of transmitted/reflected light may be chosen to be different from the 50/50 ratio indicated in the drawings.

Also shown in FIG. 1 is a shield 6 stretching towards the lens. The shield 6 extends from the transition zone between the reflecting 3A and the transparent 3B parts of the beam splitter 3, shielding the receiver 2 from the radiation emitted from the transmitter 1.

The shield and the beam-splitter may be made in one piece. Depending on the size and position of the shield it may advantageously be made in a reflecting material, reflecting radiation which otherwise would be lost, as usable radiation into the beam path or to the receiver.

The length of the shield 6 depends, among other things, on the fields of view 7,8 of the receiver 2 or the transmitter 1. This may be adjusted using a diaphragm (not shown) positioned between the transducers and the beam splitter. Preferably the diaphragm is positioned between the transducers and the beam splitter. This is to reduce the-receivers field of view, so that the length of the shield may be reduced.

The shield 6 may reach the lens or lens system, dividing the internal space of the sensor system in two, and thus making an effective protection for the receiver, but this limits the effective aperture of the lens 4, and thus the energy received by the receiver 2. The length of the shield 6 is therefore be chosen according to the specified use in different situations.

The transducers 1, 2 may comprise optical devices, such as filter, lenses and/or beam splatters to combine or divide for example light with different wavelengths from or to different transducers. Also, calibrating systems may be included e.g. to optionally allow transmitting of light directly from the transmitter to the receiver, possibly by a separate reference channel, to measure the spectrum of the emitted radiation.

The system according to the invention also includes standard equipment, such as power supply and control circuits, not shown in the drawings and common in similar sensor systems.

What is claimed is:

1. A sensor system for measuring the light absorption in a target, comprising:
   a light source adapted to emit light within a chosen range of wavelengths;
   a light receiver adapted to detect light within a chosen range of wavelengths,
   a partially reflective beam splitter adapted to transmit light from said light source, and to reflect light to said light receiver,
   a lens with a chosen focal length transmitting light between said light source and said light receiver, characterized in that the beam splitter comprises a first reflecting part and a second transmitting part being different from said first reflecting part, and
   a shield being positioned between said transmitting part and said light source, and that said first reflecting part of the beam splitter is positioned closer to said light source than said second part of the beam splitter, the shield protruding from a border between said parts towards said lens.

2. A sensor system according to claim 1, characterized in that the light source and the light receiver are both positioned proximate to the focal point of said lens.

3. A sensor system according to claim 1, characterized in that the beam splitter comprises a mirror positioned in part of an aperture of said lens.

4. A sensor system according to claim 1, characterized in that the shield and the reflecting part of the beam splitter comprises a plate and a mirror given a chosen angle in relation to the plate.

5. A sensor system according to claim 1, characterized in that the sensor system further comprises a diaphragm positioned between the light source and the light receiver and the beam splitter, reducing a field of view of the light source and the light receiver, and reducing the required length of the shield.

6. A sensor system according to claim 1, characterized in that the shield is made of a reflecting material.

7. A sensor system for measuring the light absorption in a target, comprising:
   a light source adapted to emit light within a chosen range of wavelengths;
   a light receiver adapted to detect light within a chosen range of wavelengths,
   a partially reflective beam splitter adapted to reflect light from said light source, and to transmit light to said light receiver,
   a lens with a chosen focal length transmitting light between said light source and said light receiver, characterized in that the beam splitter comprises a first reflecting part and a second transmitting part being different from said first reflecting part, and
   a shield being positioned between said transmitting part and said light source,
   said first reflecting part of the beam splitter being positioned closer to said light source than said second part of the beam splitter, the shield protruding from a border between said parts towards said lens.

8. A sensor system according to claim 7, characterized in that the light source and the light receiver are both positioned proximate to the focal point of said lens.

9. A sensor system according to claim 7, characterized in that the beam splitter comprises a mirror positioned in part of an aperture of said lens.

10. A sensor system according to claim 7, characterized in that the shield and the reflecting part of the beam splitter comprises a plate and a mirror given a chosen angle in relation to the plate.

11. A sensor system according to claim 7, characterized in that the sensor system further comprises a diaphragm positioned between the light source and the light receiver and the beam splitter, reducing a field of view of the light source and the light receiver, and reducing the required length of the shield.

12. A sensor system according to claim 7, characterized in that the shield is made of a reflecting material.

* * * * *